(12) United States Patent
Callahan et al.

(10) Patent No.: US 7,866,471 B2
(45) Date of Patent: Jan. 11, 2011

(54) MEDICAL SYSTEM WITH SKIN APPLICATOR

(75) Inventors: Mark J. Callahan, Medway, MA (US); Steven A. Holley, West Roxbury, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 32 days.

(21) Appl. No.: 12/365,422

(22) Filed: Feb. 4, 2009

(65) Prior Publication Data

US 2010/0198166 A1   Aug. 5, 2010

(51) Int. Cl.
*A61B 19/02* (2006.01)

(52) U.S. Cl. ............... 206/438; 206/216; 206/223; 206/229; 220/735; 220/736

(58) Field of Classification Search .......... 206/38, 206/216, 223, 229, 230, 363, 370, 438, 570, 206/828; 220/735, 736, 570
See application file for complete search history.

(56) References Cited

U.S. PATENT DOCUMENTS

| D46,262 | S | 8/1914 | Meinecke |
| 1,607,865 | A * | 11/1926 | Butler ............... 206/542 |
| 3,324,855 | A | 6/1967 | Heimlich et al. |
| 3,399,020 | A | 8/1968 | Margolis et al. |
| D216,958 | S | 3/1970 | Dallaire |
| D217,409 | S | 4/1970 | Ott |
| 3,519,364 | A | 7/1970 | Truhan |
| D219,323 | S | 11/1970 | Bost |
| 3,601,287 | A | 8/1971 | Schwartzman |
| 3,636,922 | A | 1/1972 | Ketner |
| 3,851,649 | A * | 12/1974 | Villari ............... 206/438 |
| 3,891,331 | A | 6/1975 | Avery |
| 3,992,729 | A | 11/1976 | Mills |
| 4,080,968 | A | 3/1978 | Nielsen |
| 4,084,910 | A | 4/1978 | LaRosa |
| D249,162 | S | 8/1978 | Mills |
| 4,140,409 | A | 2/1979 | DeVries |
| 4,148,318 | A | 4/1979 | Meyer |
| 4,173,978 | A | 11/1979 | Brown |
| 4,183,684 | A | 1/1980 | Avery, Jr. |
| 4,201,491 | A | 5/1980 | Kohler |
| 4,225,254 | A | 9/1980 | Holberg et al. |
| 4,226,328 | A * | 10/1980 | Beddow ............... 206/364 |
| 4,368,548 | A | 1/1983 | Glass |
| D269,378 | S | 6/1983 | Work |
| 4,415,288 | A | 11/1983 | Gordon et al. |
| D275,606 | S | 9/1984 | Zawachi |
| 4,474,016 | A | 10/1984 | Winchell |
| 4,498,796 | A | 2/1985 | Gordon et al. |
| 4,507,111 | A | 3/1985 | Gordon et al. |
| 4,522,302 | A * | 6/1985 | Paikoff ............... 206/570 |
| 4,616,642 | A | 10/1986 | Martin et al. |
| 4,863,422 | A | 9/1989 | Stanley |
| 4,925,047 | A | 5/1990 | Valentine et al. |
| 4,925,327 | A | 5/1990 | Wirt |

(Continued)

*Primary Examiner*—Mickey Yu
*Assistant Examiner*—Chun Cheung
(74) *Attorney, Agent, or Firm*—Lisa E. Winsor, Esq.

(57) ABSTRACT

A medical system 10 may include a fluid basin 100, a medical skin applicator, an aspirator instrument, gauze pads 400, sponges 500 and medicinal container 600. Each may be stored within the fluid basin 100 during transport of the medical system 10.

7 Claims, 7 Drawing Sheets

U.S. PATENT DOCUMENTS

| | | | |
|---|---|---|---|
| 4,954,239 A * | 9/1990 | Mueller | 206/571 |
| 5,006,004 A | 4/1991 | Dirksing et al. | |
| 5,015,228 A | 5/1991 | Columbus et al. | |
| 5,019,033 A | 5/1991 | Geria | |
| 5,045,076 A | 9/1991 | Pierce | |
| 5,072,832 A * | 12/1991 | Valentine et al. | 206/570 |
| 5,088,849 A | 2/1992 | Johnson et al. | |
| 5,117,981 A * | 6/1992 | Crawford et al. | 206/570 |
| 5,147,337 A | 9/1992 | Plone | |
| 5,178,282 A * | 1/1993 | Williams | 206/570 |
| 5,288,159 A | 2/1994 | Wirt | |
| 5,308,180 A | 5/1994 | Pournoor et al. | |
| 5,435,660 A | 7/1995 | Wirt | |
| 5,449,071 A * | 9/1995 | Levy | 206/569 |
| 5,487,393 A | 1/1996 | Haswell et al. | |
| 5,489,280 A | 2/1996 | Russell | |
| 5,509,744 A | 4/1996 | Frazier | |
| 5,658,084 A | 8/1997 | Wirt | |
| 5,674,227 A | 10/1997 | Burns | |
| 5,697,921 A | 12/1997 | Blair | |
| 5,713,843 A | 2/1998 | Vangsness | |
| 5,769,552 A | 6/1998 | Kelley et al. | |
| 5,775,826 A | 7/1998 | Miller | |
| 5,779,053 A * | 7/1998 | Partika et al. | 206/570 |
| 5,791,801 A | 8/1998 | Miller | |
| 5,871,297 A | 2/1999 | Rogers et al. | |
| 6,190,367 B1 | 2/2001 | Hall | |
| D441,075 S | 4/2001 | Nara | |
| 6,238,117 B1 | 5/2001 | Griebel et al. | |
| 6,238,907 B1 | 5/2001 | Schuler-Maloney et al. | |
| 6,371,675 B1 | 4/2002 | Hoang et al. | |
| 6,398,062 B1 | 6/2002 | Jones | |
| 6,415,455 B1 | 7/2002 | Slaon, III et al. | |
| 6,422,778 B2 | 7/2002 | Baumann et al. | |
| 6,471,095 B1 | 10/2002 | Cann | |
| 6,488,665 B1 | 12/2002 | Severin et al. | |
| 6,505,985 B1 | 1/2003 | Hidle et al. | |
| 6,532,604 B2 | 3/2003 | Moser | |
| 6,533,484 B1 | 3/2003 | Osei et al. | |
| 6,536,975 B1 | 3/2003 | Tufts | |
| 6,595,696 B1 | 7/2003 | Zellak | |
| 6,602,230 B1 | 8/2003 | Fisher et al. | |
| 6,616,363 B1 | 9/2003 | Guillaume et al. | |
| D482,780 S | 11/2003 | Robbins et al. | |
| 6,672,784 B2 | 1/2004 | Baumann et al. | |
| 6,689,103 B1 | 2/2004 | Palasis | |
| 6,729,786 B1 | 5/2004 | Tufts et al. | |
| 6,743,211 B1 | 6/2004 | Prausnitz et al. | |
| 6,755,586 B1 | 6/2004 | Frazier | |
| 6,811,341 B2 | 11/2004 | Crane | |
| 6,869,242 B2 | 3/2005 | May | |
| 6,909,339 B2 | 6/2005 | Yonekura et al. | |
| 6,910,822 B2 | 6/2005 | Hidle et al. | |
| 6,916,137 B2 | 7/2005 | Shiraiwa | |
| 7,025,733 B2 | 4/2006 | McQuaid | |
| 7,147,626 B2 | 12/2006 | Goodman et al. | |
| 7,153,294 B1 | 12/2006 | Farrow | |
| D547,124 S * | 7/2007 | Peretz | D7/538 |
| D577,960 S * | 10/2008 | Ersan | D7/541 |
| 2001/0055511 A1 | 12/2001 | Baumann et al. | |
| 2002/0076258 A1 | 6/2002 | Crosby et al. | |
| 2003/0049069 A1 | 3/2003 | Osei et al. | |
| 2003/0060746 A1 | 3/2003 | Mark | |
| 2003/0068190 A1 | 4/2003 | Hidle et al. | |
| 2003/0118629 A1 | 6/2003 | Scholz et al. | |
| 2003/0149106 A1 | 8/2003 | Mosbey et al. | |
| 2003/0194447 A1 | 10/2003 | Scholz et al. | |
| 2004/0068218 A1 | 4/2004 | Davis et al. | |
| 2004/0162533 A1 | 8/2004 | Alley | |
| 2004/0179888 A1 | 9/2004 | Tufts et al. | |
| 2004/0240927 A1 | 12/2004 | Hoang et al. | |
| 2004/0267182 A1 | 12/2004 | Davis et al. | |
| 2005/0197638 A1 | 9/2005 | Papendick et al. | |
| 2006/0009742 A1 | 1/2006 | Solazzo | |

\* cited by examiner

MEDICAL SYSTEM WITH SKIN APPLICATOR

BACKGROUND

1. Technical Field

The present disclosure relates generally to a medical kit or system, and more particularly, relates to a medical system including a skin applicator for dispensing sterilizing fluid to a skin surface of a patient, a basin for collecting fluids and assorted additional surgical instrumentation required to perform a medical procedure.

2. Description of the Related Art

Many medical procedures involve application of medicines, sterilizing fluids, antiseptics, gels, agents or other materials to portions of the body, such as the skin, for preparation, treatment, etc. Such medicines, sterilizing fluids, agents are typically transferred to the skin via an applicator. Conventional liquid applicators incorporate a glass ampoule or plastic blow-molded bottles for storing the liquid and a mechanism for fracturing the ampoule to release the stored liquid. The released liquid contacts a swab, foam pad or tip for application to the skin.

In addition to the task of applying sterilizing fluids to the skin surface, the medical procedure typically requires performance of additional medical or surgical tasks. These tasks may include aspiration or removal of body fluids from the treatment area, collection of the body fluids, application of medicants to the treatment and other tasks.

SUMMARY

Accordingly, the present disclosure is directed to a medical system for use during a medical procedure and which incorporates a variety of instrumentation including a medical skin applicator for performing the medical procedure. In accordance with one embodiment of the present disclosure, the medical system includes a basin and a medical skin applicator mountable to the fluid basin. The basin defines a lower base and a peripheral wall depending from the lower base. The base and the peripheral wall define a reservoir for receiving body fluids. The peripheral wall has a pair of recesses therein and disposed in general opposed relation. In one embodiment, the peripheral wall includes an upper flange with the pair of recesses being disposed within the upper flange.

The medical skin applicator stores a medical agent to be dispensed relative to a subject in conjunction with the medical procedure. The medical skin applicator may include an outer housing, a fluid housing having a fluid chamber for storing the medical agent and an applicator head mounted to the outer housing for dispensing the medical agent. The medical applicator also may include an actuator mounted to the fluid housing and extending beyond the outer housing. The actuator may be received within a first recess of the fluid basin and the applicator head being received within a second recess of the fluid basin. An absorbent member may be mounted to the applicator head. The absorbent member may be at least partially received within the second recess of the fluid basin. One of the actuator and the first recess may include a locking rib, and the other of the actuator and the first recess may include a corresponding locking recess. The locking rib and the locking recess cooperate to minimize potential of movement of the actuator relative to the outer housing during transit.

The applicator head of the medical applicator may include a penetrating member. The actuator may be movable from an initial transit condition to an activated condition to cause corresponding relative movement between the fluid housing and the penetrating head whereby the penetrating head penetrates the fluid housing and causes release of the medical agent.

The medical system further may include at least one of an aspiration instrument, gauze, sponge or medicinal container. Any or all of these components may be stored within the fluid basin.

The medical system provides an effective mechanism to transport and store a fluid basin, medical skin applicator and assorted instrumentation, which may be utilized during a medical procedure.

In accordance with another embodiment, the medical system includes a basin and a medical applicator mountable to the basin. The basin defines a lower base and a peripheral wall depending from the lower base. The base and the peripheral wall define a reservoir for receiving body fluids. The medical applicator includes an outer housing, a fluid housing having a fluid chamber containing a medical agent to be dispensed relative to a subject and an applicator head mounted to the outer housing for dispensing the medical agent. The applicator head includes an internal penetrating member. An absorbent member is mounted to the applicator head. An actuator is mounted to the fluid housing and extends beyond the outer housing. The actuator is movable from an initial transit condition to an activated condition to cause corresponding relative movement between the fluid housing and the penetrating head whereby the penetrating head penetrates the fluid housing and causes release of the medical agent through the applicator head and to the absorbent member. The fluid housing may include a penetrable liner which is penetrated by the penetrating head upon movement of the actuator from the initial transit condition to the activated condition.

The peripheral wall of the basin may include first and second recesses therein and disposed in general opposed relation. The actuator of the medical applicator may be dimensioned to be received within the first recess of the fluid basin and the applicator head may be dimensioned to be received within the second recess of the fluid basin when the actuator is in the initial transit condition. The peripheral wall of the basin may include an upper flange. The upper flange has the first and second recesses.

BRIEF DESCRIPTION OF THE PREFERRED DRAWINGS

Preferred embodiments of the present disclosure will be better understood by reference to the drawings wherein.

DETAILED DESCRIPTION OF THE EMBODIMENTS

The exemplary embodiments of the medical system and use(s) thereof will be discussed in conjunction with a medical procedure incorporating, at least in part, a medical skin applicator for application of sterilizing fluids, gels or agents to the skin of a body for preparation, treatment, etc. The medical system and associated procedure further incorporates instrumentation and products which may be utilized with the medical procedure. Such instrumentation or products are inclusive of, but, not limited to, an aspiration instrument, gauze pads, a medicinal container, sponges and a fluid basin. The fluid basin also stores these instruments during transport and collects fluid removed from the subject.

In the discussion that follows, the term "proximal" will refer to the portion of a structure that is closer to a practitioner, while the term "distal" will refer to the portion that is further from the practitioner or user. As used herein, the term "subject" refers to a human patient or other animal. According to the present disclosure, the term "practitioner" or "user" refers typically to a doctor, nurse or other care provider and may include support personnel.

Figure 1:
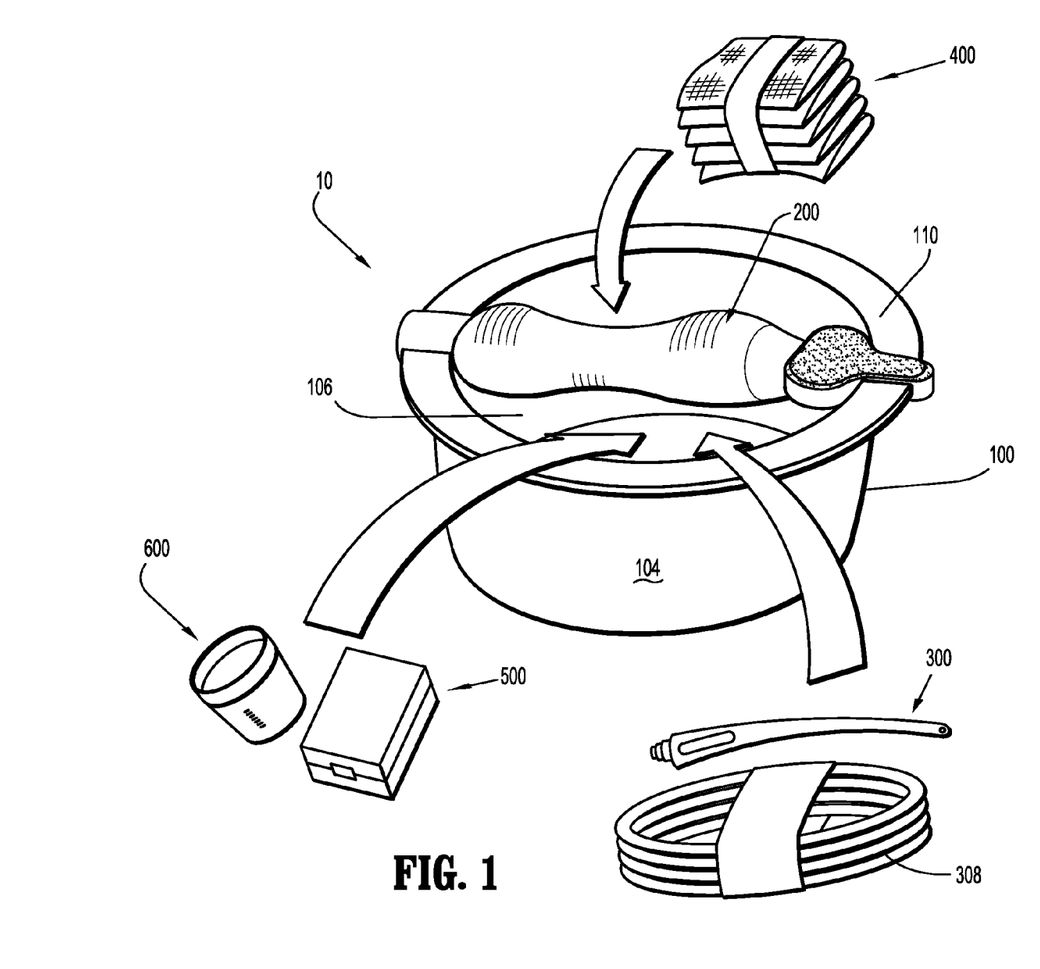
FIG. 1 is a perspective view of the medical kit or system in accordance with the principles of the present disclosure including a skin applicator apparatus, fluid collection basin and various of instrumentation and items to be used in performance of a medical procedure.

Referring now to FIG. 1, there is illustrated, in perspective, the medical kit or system in accordance with the principles of the present disclosure. Medical system 10 includes fluid basin 100, medical skin applicator apparatus 200, aspirator instrument 300, gauze pads 400, sponges 500 and medicinal container 600, all of which are stored within fluid basin 100 during transport of medical system 10. Medical system 10 may include more or less of these components or include additional components or instruments. Other medical instruments are envisioned including syringes, catheters or the like.

Fluid basin 100 is intended to accumulate or collect saline, blood, urine, irrigation fluids, exudates, saliva or the like which may be presented during the performance of a medical or surgical procedure. Such elements will be hereinafter collectively referred to as "fluids". Fluid basin 100 may also accommodate various tissue or organs removed during the procedure. Fluid basin 100 may also store instrumentation of the medical system 10 during transit and/or storage.

Returning to FIGS. 1 and 2, fluid basin 100 may be manufactured from stainless steel, aluminum or alloys thereof, or, alternatively, of a suitable polymeric material and be formed by any known manufacturing, molding, or processing techniques. Several molding techniques include thermal molding or rotational molding, or any other known injection molding technique. Examples of suitable polymeric materials include polycarbonates, polystyrenes, polyacrylates, polypropylene or polyethylene. As a further alternative, fluid basin 100 may be formed of natural biogenic polymers such as cellulose and may be biodegradable. Fluid basin 100 may be translucent at least through a portion of the basin 100. Fluid basin 100 is preferably disposable, i.e., is intended to be disposed after a single use; however, it is envisioned that the fluid basin 100 may be sterilized after each use if formed of a suitable sterilizable metal material.

Figure 2:
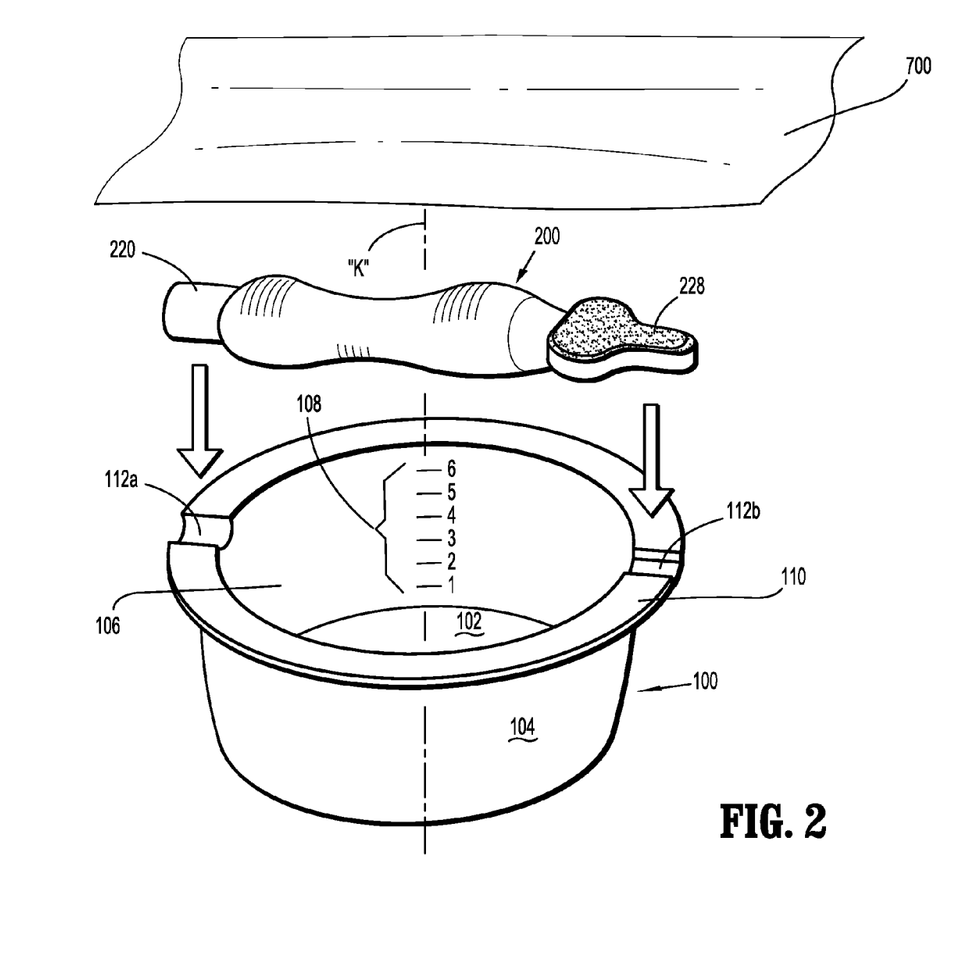
FIG. 2 is a perspective view illustrating the basin and the skin applicator of the medical system of FIG. 1.

Fluid basin 100 includes lower base or floor 102 and outer peripheral wall 104 extending contiguously from the lower wall 102 and being arranged about longitudinal axis "k". Fluid basin 100 defines internal chamber 106 within the boundaries of lower floor 102 and peripheral wall 104. Fluid basin 100 may be of various configurations or shapes. In one embodiment, fluid basin 100 is generally circular when viewed from the top. Fluid basin 100 may include indicia markings 108 incorporated within peripheral wall 104 to assist the practitioner in determining the volume of fluids within the fluid basin 100. The indicia markings 108 may include written indicia corresponding to the predetermined fluid volume. The written indicia may be in the form of numerical and/or text symbols, visual symbols or the like, which are written, drawn, engraved or molded into peripheral wall 26.

Fluid basin 100 further includes lip or flange 110 extending from peripheral wall 104. Upper flange 110 is annular in configuration and is arranged in a plane transverse, i.e. perpendicular to longitudinal axis "k". Other angular orientations or arrangements of upper flange 110 are also envisioned. For example, upper flange 110 may reside in a plane obliquely arranged with respect to the longitudinal axis "k". Upper flange 110 provides increased structural support to fluid basin 100. Upper flange 110 further may include a pair of recesses 112a, 112b in its upper surface. Recesses 112a, 112b may be in diametrical opposed relation with respect to the longitudinal axis "k" and define holding grooves for supporting medical applicator apparatus 200 as will be further discussed hereinbelow. In this regard, upper flange 110 defines a support surface for retaining and presenting medical applicator apparatus 200 in a predetermined orientation. In the alternative, fluid basin 100 may be devoid of upper flange 110 whereby the upper surface of peripheral wall 104 is the support surface and may possess the pair of recesses 112a, 112b for accommodating medical applicator apparatus 200.

Figure 3:
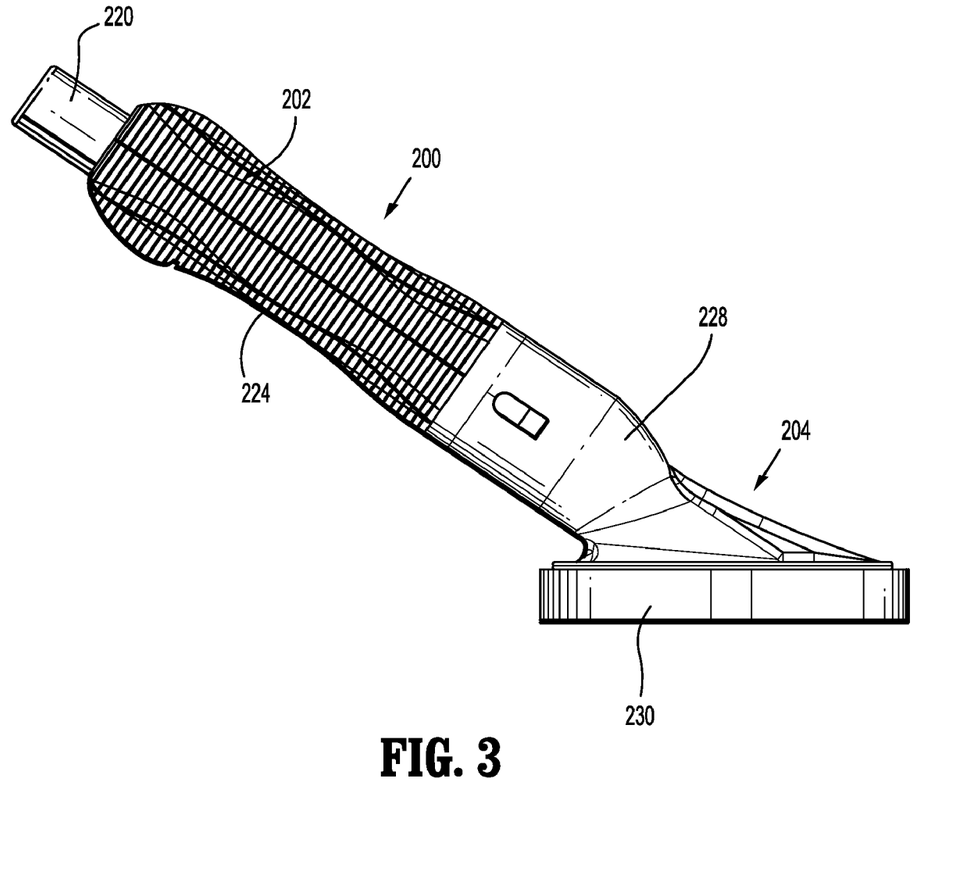
FIG. 3 is a side plan view of the skin applicator.
Figure 4:
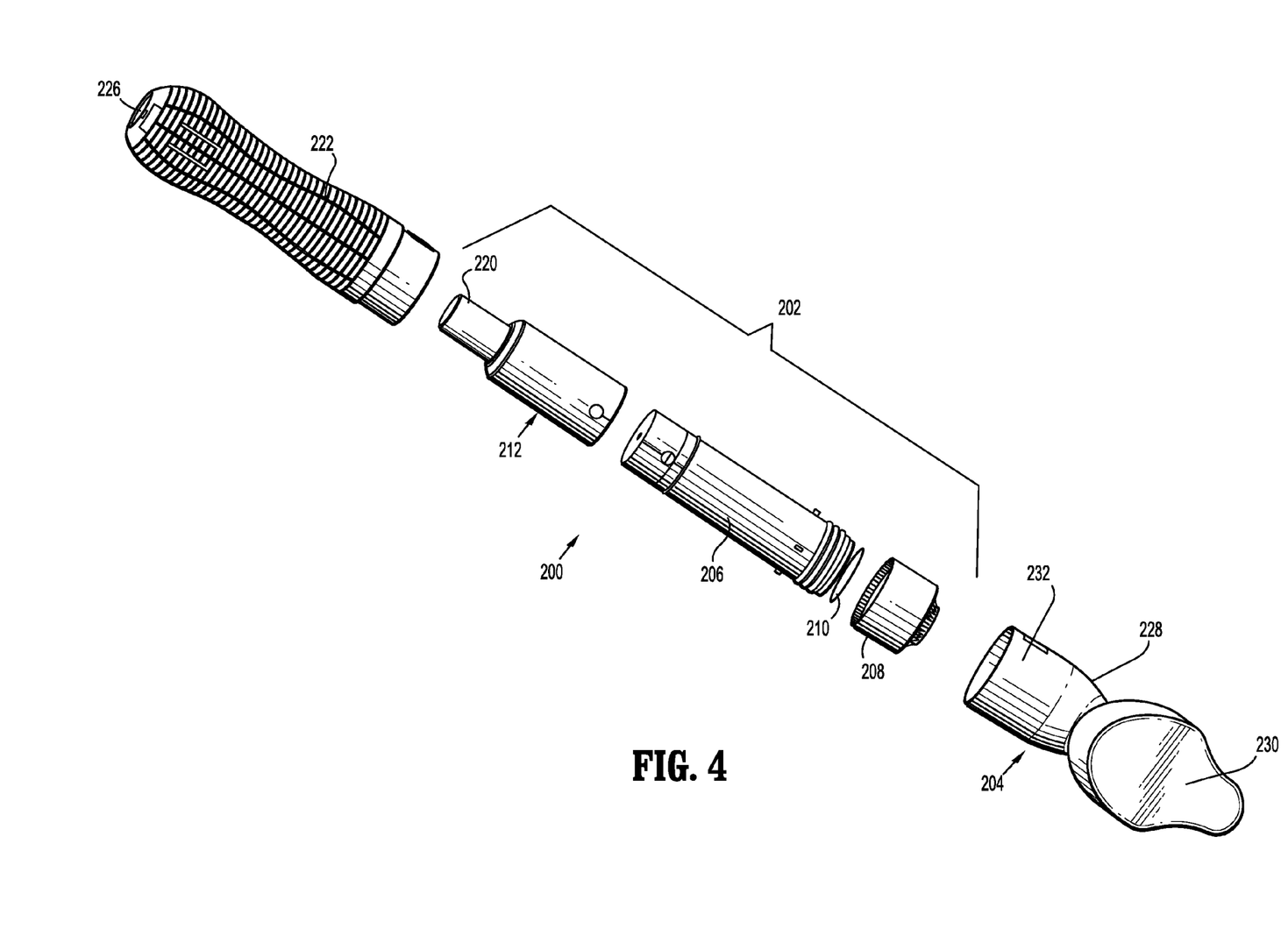
FIG. 4 is a perspective view with parts separation of the skin applicator of FIG. 3.
Figure 5:
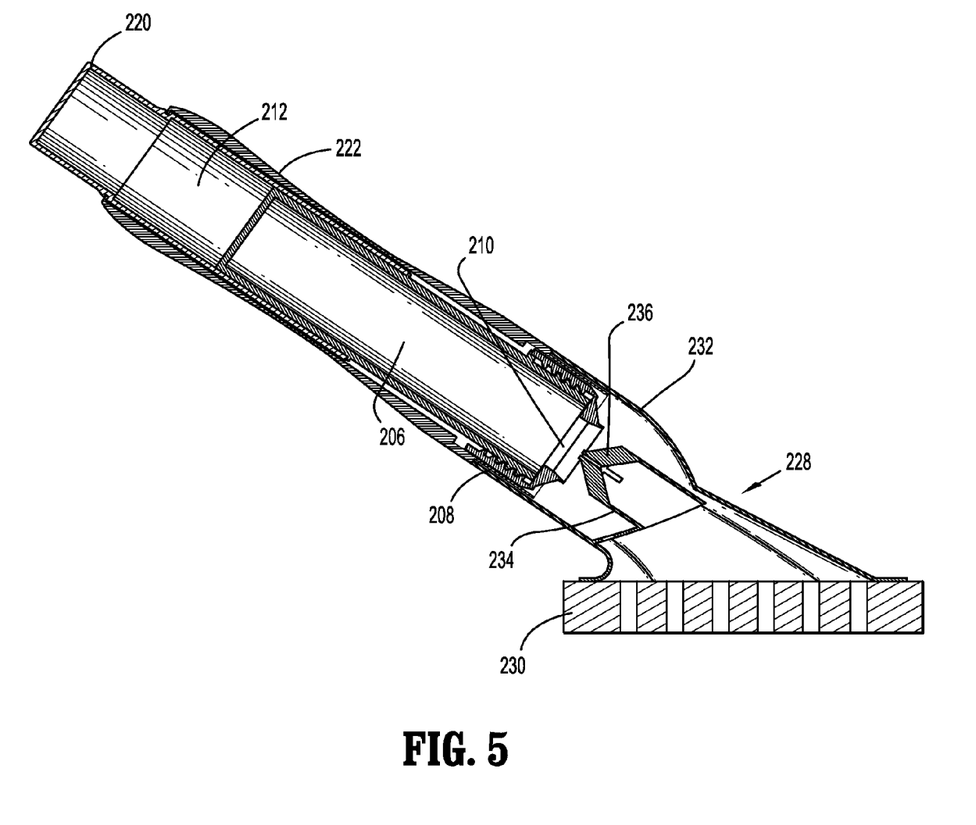
FIGS. 5-6 are side cross-sectional views of the skin applicator in a first transition position and a second actuated position, respectively.

Referring now to FIGS. 3-5, skin applicator apparatus 200 will be discussed. This medical applicator apparatus 200 may be substantially similar to the skin applicator apparatus disclosed in commonly assigned U.S. Patent Publication No. 2006/0039742A1 to Cable et al., the entire contents of which are hereby incorporated by its entirety by reference herein. Skin applicator 200 includes fluid container assembly 202 and applicator head assembly 204 connected to the fluid container assembly 202. Fluid container assembly 202 includes fluid housing 206, end cap 208 connected to the housing 206 and foil liner 210. Fluid housing 206 defines an internal chamber which is filled with a medicants, cleaning solution or the like. Such medicants are inclusive of antiseptic solutions, sterilizing solutions, in liquid or gel form.

Fluid container assembly 202 further includes housing extension 212 which is connected to fluid housing 206. Housing extension 212 further defines manually engageable actuator 220 at its proximal end. Actuator 220 defines a reduced diameter relative to the remaining portion of housing extension 212.

Skin applicator 200 further includes outer housing 222. Outer housing 222 is secured to applicator head assembly 204 and is dimensioned to accommodate fluid housing 206 and housing extension 212. Outer housing 222 defines a contoured configuration having a plurality of spaced ribs 224 on its outer surface to facilitate gripping engagement by the practitioner. Outer housing 222 defines central aperture 226 at its proximal end which receives manually engageable actuator 220 of housing extension 212. Actuator 220 and housing extension 212 is adapted to move in a general longitudinal direction relative to outer housing 222.

Applicator head assembly 204 includes applicator frame 228 and absorbent applicator member 230 attached to the applicator frame 228. Applicator frame 228 includes throat 232 defining an internal bore for reception of end cap 208 and fluid housing 206. Throat 232 is fixed to outer housing 222.

The interior of throat 232 includes an internal collar 234 and a plurality of penetrating members 236 extending from the internal collar 234. Penetrating members 236 pierce liner 210 when fluid housing 206 is advanced relative to outer housing 222 to release the antiseptic fluid within fluid housing 206 for dispensing in absorbent applicator member 230. Absorbent applicator member 230 may comprise foam or the like and defines a general tear-drop shape having an enlarged section 238 and an elongated neck or prow section 240. Prow section 240 defines a narrow profile to assist in maneuvering within accessible areas.

Figure 6:
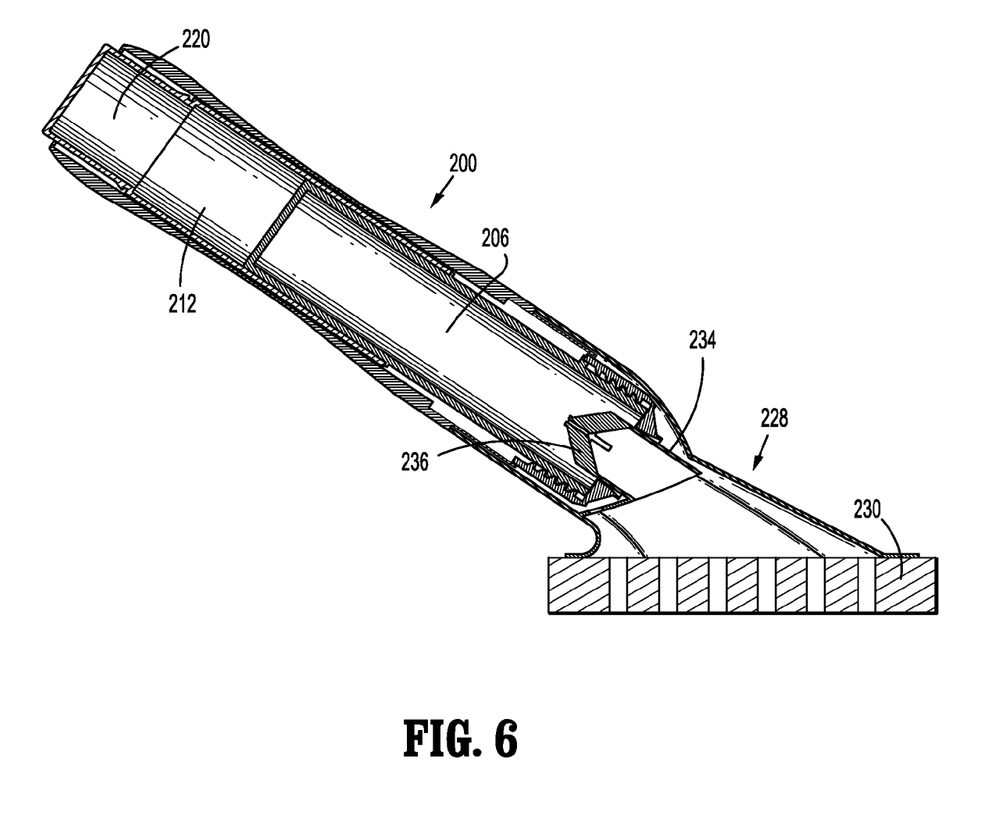

FIG. 5 illustrates medical applicator apparatus 200 in an initial transit condition. Medical applicator apparatus 200 is in the initial transit condition when stored within fluid basin 100 as depicted in FIG. 1. When it is desired to use medical applicator 200, the practitioner removes medical applicator apparatus 200 from fluid basin 100. The practitioner will advance actuator 220 at the proximal end of housing extension 212 with the heel of his hand or, alternatively, with the thumb of the practitioner. Distal movement of actuator 220 and fluid housing 206 from the initial transit condition of FIG. 5 to the second activated condition of FIG. 6 causes liner 210 to be penetrated by the four penetrating members 236. The antiseptic solution thus passes from fluid housing 206 through internal collar 234 and into applicator member 230 for application to the patient.

Further details of the use of skin applicator apparatus may be ascertained by references to the Cable '742 application.

Figure 7:
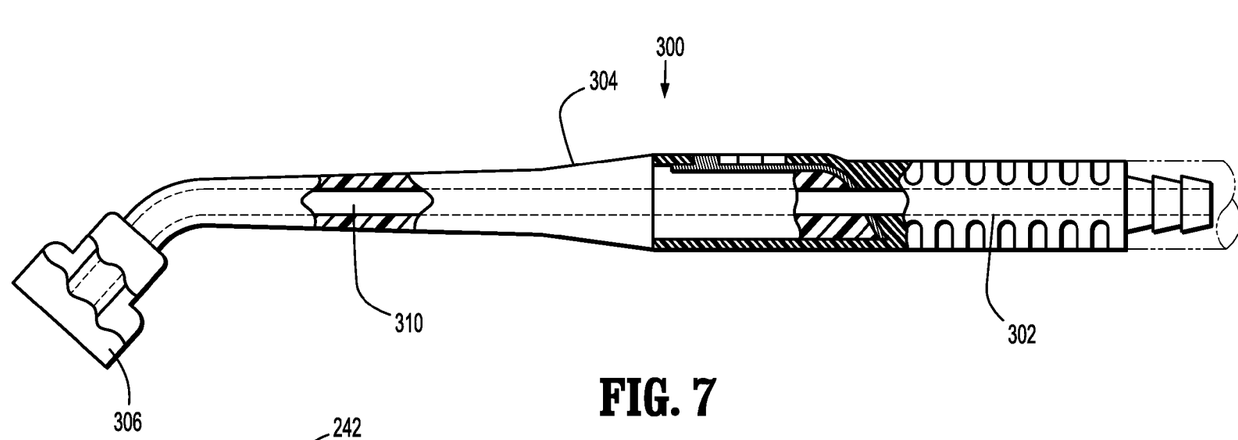
FIG. 7 is a view of the aspiration instrument of the medical system.

Referring now to FIG. 7, in conjunction with FIG. 1, aspiration instrument 300 of medical system 10 will be discussed. One suitable aspiration instrument for use with medical system is disclosed in commonly assigned U.S. Patent Publication No. 2008/0045885 to Callahan, the entire contents of such disclosure being incorporated herein by reference. Aspiration instrument 300 is contemplated for use in medical procedures requiring the aspiration of fluids of differing viscosities and compositions from body cavities. Examples of fluids of this type include blood, tissue fluid, tissue fragments, bone fragments, and rinsing fluids. Aspiration instrument 300 consists of handle 302, elongated body member 304 extending from handle 302, and compliant protective guard 306 operatively connected with the end of the body member 304. In one preferred embodiment, handle 302 and body member 304 are individual components, however, the handle and the body member may also be integrated to form a single unit. Aspiration instrument 300 may be formed of polymeric material and other plastics. Alternatively, application instrument may be manufactured from a biocompatible metal such as titanium or stainless steel. Aspiration instrument 300 is operably connectable to a vacuum source through the use of tubing 302. Aspiration instrument 300 defines a longitudinal passageway 310 for drawing a vacuum to remove the fluids.

With reference again to FIG. 2, medical system further includes a roll of gauze or gauze pads 400. Suitable gauze pads include KERLIX® AMD gauze commercially available by TycoHealthcare (d/b/a Covidien). Medical sponges 500 of medical system 10 may be any polymeric and/or cellular sponge. Medicinal container 600 may contain a variety of medicants, antibiotics, treatment solutions or the like used in connection with the medical procedure.

Referring again to FIGS. 1-2, the assembly of medical system 10 will be discussed. The various devices including aspiration instrument 300 and tubing 308, gauze pads 400, sponges 500 and medicinal container 600 are positioned within fluid basin 100. These components may be secured within fluid basin 100 with the use of foam or other packing material. Thereafter, applicator apparatus 200 is positioned whereby actuator 220 is received within recess 112a of upper flange 110 and elongated neck or prow section 240 of absorbent applicator member 230 is received within second recess 112b. When mounted, actuator 220 of medical applicator apparatus 200 does not extend or will only extend a minimum distance beyond flange 110 to minimize the potential of any movement of the actuator 220 relative to outer housing 222. This will minimize potential of accidental activation of the medical applicator apparatus 200. In one embodiment, actuator 220 and applicator frame 228 and/or prow section 240 are dimensioned to establish a friction fit within corresponding recesses 112a, 112b to secure medical applicator apparatus 200 relative to basin 100. Other arrangements are also envisioned including a snap fit relation where inner surfaces defining recesses 112a, 112b flex to receive medical applicator apparatus 200 and, then, return under their own resiliency to secure respective components of the medical applicator apparatus in a releasably secured relation. Once assembled, a shrink wrap or plastic wrapping 700 may be positioned over at least the top of fluid basin to secure the components.

Figure 8:
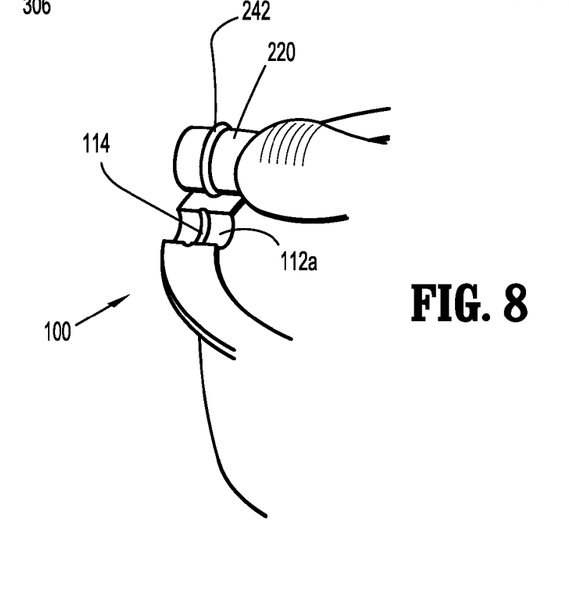
FIG. 8 is a view of a supplemental mechanism for securing the skin applicator relative to the fluid basin.

FIG. 8 illustrates an alternative embodiment where fluid basin 100 includes a supplemental recessed surface 114 within recess 112a. Actuator button 220 of medical applicator apparatus 200 includes a corresponding circumferential locking rib 242 which is positioned within recess 114 when medical applicator apparatus 200 is mounted to fluid basin 100. The interaction of supplemental recessed surface 114 and locking rib 242 further may minimize the potential of activation of skin applicator 200 through the potential inadvertent advancement of actuator 220 and fluid housing 206 relative to outer housing 222 of medical applicator apparatus 200. It is also envisioned that actuator 220 may include a recess and skin applicator 200 may include a locking rib within recess 112a.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A medical system, which comprises:
   a basin defining a lower base and a peripheral wall depending from the lower base, the basin defining an open end, the base and the peripheral wall defining a reservoir for receiving body fluids, the peripheral wall having first and second recesses therein adjacent the open end, the first and second recesses leading to and communicating with the reservoir;
   a medical applicator including:
      an outer housing;
      a fluid housing having a fluid chamber containing a medical agent to be dispensed relative to a subject;
      an applicator head mounted to the outer housing for dispensing the medical agent, the applicator head including an internal penetrating member;
      an absorbent member mounted to the applicator head;
      an actuator mounted to the fluid housing and extending beyond the outer housing, the actuator being movable from an initial transit condition to an activated condition to cause corresponding relative movement between the fluid housing and the penetrating head whereby the penetrating head penetrates the fluid housing and causes release of the medical agent through the applicator head and to the absorbent member; and the medical applicator mounted to the basin with the actuator at least partially accommodated within the first recess of the peripheral wall and the applicator head at least partially accommodated within the second recess of the peripheral wall, the medical applicator being releasable from the basin for use in a surgical procedure.

2. The medical system according to claim 1 wherein the fluid housing includes a penetrable liner, the penetrable liner being penetrated by the penetrating head upon movement of the actuator from the initial transit condition to the activated condition.

3. The medical system according to claim 1 wherein the peripheral wall includes an upper flange, the upper flange having the first and second recesses.

4. The medical system according to claim 1, wherein the actuator is dimensioned to not extend beyond the peripheral wall of the basin when in the initial condition thereof and mounted to the basin.

5. The medical system according to claim 3, wherein the actuator is dimensioned to not extend beyond the upper flange when in the initial condition thereof and mounted to the basin.

6. The medical system according to claim 1 wherein one of the actuator and the first recess includes a locking rib, and the other of the actuator and the first recess includes a corresponding locking recess, the locking rib and the locking recess cooperating to minimize potential of movement of the actuator relative to the outer housing.

7. The medical system according to claim 1 including at least one of an aspiration instrument, gauze, sponge or medicinal container, the at least one being stored within the fluid basin.

\* \* \* \* \*